US009245335B2

(12) United States Patent
Jouhikainen (10) Patent No.: US 9,245,335 B2
(45) Date of Patent: Jan. 26, 2016

(54) METHOD AND SYSTEM FOR CONTROLLING COMPUTER TOMOGRAPHY IMAGING (75) Inventor: Petri Jouhikainen, Jarvenpaa (FI)

(73) Assignee: PaloDEx Group Oy, Tuusula (FI)

( * ) Notice: Subject to any disclaimer, the term of this patent is extended or adjusted under 35 U.S.C. 154(b) by 278 days.

(21) Appl. No.: 13/820,671

(22) PCT Filed: Sep. 6, 2011

(86) PCT No.: PCT/FI2011/050766
§ 371 (c)(1),
(2), (4) Date: Mar. 29, 2013

(87) PCT Pub. No.: WO2012/032220
PCT Pub. Date: Mar. 15, 2012

(65) Prior Publication Data
US 2014/0147001 A1 May 29, 2014

(30) Foreign Application Priority Data
Sep. 8, 2010 (FI) ...................................... 20105934

(51) Int. Cl.
G06K 9/00 (2006.01)
A61B 6/14 (2006.01)
G06T 7/00 (2006.01)
A61B 6/00 (2006.01)
G06K 9/32 (2006.01)

(52) U.S. Cl.
CPC ................. *G06T 7/0012* (2013.01); *A61B 6/14* (2013.01); *A61B 6/545* (2013.01); *G06K 9/3241* (2013.01)

(58) Field of Classification Search
USPC ......... 382/100, 103, 106, 128–132, 154, 168, 382/173, 181, 193, 199, 219, 232, 254, 274, 382/276, 286–291, 305, 312, 319; 378/11, 378/21, 39, 208, 170, 38
See application file for complete search history.

(56) References Cited

U.S. PATENT DOCUMENTS 4,907,251 A * 3/1990 Mork ........................ A61B 6/14
378/170
6,118,842 A * 9/2000 Arai ........................ A61B 6/032
378/38

(Continued)

FOREIGN PATENT DOCUMENTS

| WO | 2009133896 | 11/2009 |
| WO | 2009133937 | 11/2009 |
| WO | 2009138483 | 11/2009 |

OTHER PUBLICATIONS

International Search Report and Written Opinion, PCT/FI2011/050766, mailed Mar. 27, 2012.

(Continued)

*Primary Examiner* — Seyed Azarian
(74) *Attorney, Agent, or Firm* — Andrus Intellectual Property Law, LLP (57) ABSTRACT A method, a device, a system and a computer program are for controlling limited-area computer tomography imaging. The method includes determining location data of a first imaging object when the first imaging object is positioned in an imaging area, determining reference location data related to the first imaging object and adjusting the imaging area based on the location data of the first imaging object and said reference location data for imaging a second imaging object. The first and the second imaging object can be located at a distance determined by the reference location data from each other or symmetrically in relation to the reference location data.

30 Claims, 4 Drawing Sheets (56) References Cited

U.S. PATENT DOCUMENTS

2002/0122537 A1* 9/2002 Yoshimura ........... A61B 6/0478
378/208
2004/0247069 A1 12/2004 Arai
2011/0044520 A1* 2/2011 Nakai .................... A61B 6/032
382/131
2012/0039435 A1* 2/2012 Arai ........................ A61B 6/06
378/11

OTHER PUBLICATIONS

Finnish Search Report, Finnish Patent Application No. 20105934, mailed Apr. 21, 2011.

Japanese Office Action in corresponding JP Appln. No. 2013-527653 issued May 7, 2015.

* cited by examiner

METHOD AND SYSTEM FOR CONTROLLING COMPUTER TOMOGRAPHY IMAGING

CROSS REFERENCE TO RELATED APPLICATIONS

The present application is the U.S. national stage application of International Application PCT/FI2011/050766, filed Sep. 6, 2011, which international application was published on Mar. 15, 2012 as International Publication WO 2012/032220. The International Application claims priority of Finnish Patent Application 20105934, filed Sep. 8, 2010. The priority PCT and Finnish patent applications are hereby incorporated herein by reference.

The invention relates to a method, a device and a system for controlling X-ray imaging. The present invention particularly relates to controlling limited-area computer tomography imaging performed in the teeth and jaw area.

TECHNICAL BACKGROUND

The imaging of the teeth and jaw area employs the so-called limited-area computer tomography devices, an example of which are cone-beam computed tomography imaging devices (CBCT). The device transilluminates the patient's skull by a beam in order to collect volume element data at a desired point in the skull and a three-dimensional image is reconstructed of the skull point in question based on the data produced. The devices are used in the teeth and jaw area specialty in diagnosing and planning treatment e.g. in procedures related to surgery, implantology and oral pathology.

An X-ray apparatus employed in limited-area computer tomography imaging typically comprises a rotating arm attached at one end of a supporting frame, at opposite ends of which are attached a device generating X-rays and a device detecting X-rays. Exposure to X-rays is performed by rotating the rotating arm, whereby the movements of the rotating arm and thus also the device generating X-rays and the device detecting X-rays are synchronised such that an image of an area of desired size e.g. of the patient's tooth or jaw joint is provided to the device detecting X-rays. Typically, the rotating arm is rotated around its stationary rotation axis. The device detecting X-rays is e.g. a CCD (charged coupled device) or a CMOS sensor which registers radiation having penetrated the object being imaged.

The diameter of the area being imaged is typically only a part of the diameter of the whole skull or jaw area. In X-ray imaging, it is important to position the imaging area of the object to be imaged precisely in a correct location in relation to the imaging apparatus. For imaging, it is also important that the object remains stationary. The positioning of the imaging area—and simultaneously the positioning of the patient to be imaged—is started by choosing and locating the object to be imaged, which can be assisted by using e.g. pointers and indicators implemented by lights or e.g. another X-ray image taken of the object.

For instance, from specification U.S. Pat. No. 6,118,842 is known an X-ray apparatus applicable for limited-area computer tomography imaging, where between the device generating X-rays and the device detecting X-rays is located an object positioning means for positioning the object to be imaged in the imaging area. In relation to their locations, the object positioning means, the device generating X-rays and the device detecting X-rays are relatively adjustable in the anteroposterior, lateral and vertical directions. From specification U.S. Pat. No. 6,118,842 is also known an X-ray apparatus for limited-area computer tomography imaging, where the location of the object positioning means positioned between the device generating X-rays and the device detecting X-rays is adjustable in relation to the frame of the X-ray apparatus in the anteroposterior, lateral and vertical directions. Then, the imaging area is located on a straight line according to the rotation axis of the rotating arm, around which the device generating X-rays and the device detecting X-rays rotate. The precise location of the object positioning means in said directions can be adjusted by an adjustment mechanism which is installed between the frame of the X-ray apparatus and the object positioning means. When adjusting the location of the object positioning means, it is possible to utilise object positioning data which has been obtained from a tomographic image taken earlier of the object by panoramic imaging. The adjustment of the location of the object positioning means can also utilise a light beam sent by a light indicator located on the rotation axis of the rotating arm, whereby the imaging area of the object is precisely in the correct place when the light beam focuses on the object positioning means or the object being imaged.

In the above limited-area computer tomography devices according to prior art, the object to be imaged is chosen one by one and the object to be imaged is positioned in the imaging area by the object positioning means one by one before performing the actual X-ray imaging. Then, a new object to be imaged is chosen and it is positioned in the imaging area by the object positioning means, after which the actual X-ray imaging is performed. The positioning of the imaging area is thus performed as its own separate measure for each object chosen to be imaged. Each object being imaged is imaged to imaging-specific coordinates determined by the positioning of the imaging area.

When wishing to use the prior-art apparatus to image e.g. the patient's both jaw joints, the first jaw joint to be imaged is first positioned by the object positioning means in its place in the imaging area, after which it is imaged, and then the second jaw joint to be imaged is positioned by the object positioning means in its place in the imaging area, after which it is imaged. In order to be able to image both jaw joints, the patient being imaged has to be positioned twice by the object positioning means to the imaging area, because both jaw joints are imaged separately. Each separate positioning of the patient for imaging takes time and consumes human and device resources. Furthermore, when the patient being imaged is positioned twice by the object positioning means to the imaging area for imaging the jaw joints, both jaw joints are imaged in their own coordinates. After this as an additional step, both images have to be registered in one way or another in the same coordinates before being able to make comparisons and measurements between the objects having been imaged. When the separately shot images are registered in the same coordinates, extra auxiliary means are required, the dimensions and geometry of which are known and which are visible in both images, or the images must have a common area which is visible in both images.

A problem of the above arrangements is also that they do not in any way consider the special characteristics related to the location or the resemblances of the object to be imaged. The human body has e.g. several imagable objects which are located in pairs on both sides of the body. Often, the imaging need relates to both such objects in order to be able to compare possible differences in the objects. Such objects in the human body are e.g. the above-mentioned jaw joints which are symmetrically located on two sides of the skull. When imaging by prior-art devices, both jaw joints must be positioned in the imaging area and imaged separately, whereby two positioning periods for positioning the imaging area are required to image the jaw joints. The two separate positionings of the imaging area also cause the fact that the jaw joints are imaged in different coordinates, the registering of which in the same coordinates requires the above-mentioned additional measures. Thus, imaging particularly objects located symmetrically on different sides of the body or the skull is slow and awkward.

SUMMARY

An object of the invention is to eliminate disadvantages related to the prior art. According to an object, the invention aims at simplifying and speeding the work flow of computer tomography imaging. A particular object of the invention is to speed up object positioning for computer tomography imaging when the objects to be imaged are located e.g. symmetrically on two sides of the human body. According to an additional object, the invention aims at diversifying the possible uses of X-ray image data.

An object of the invention is provided by a method according to claim 1, an object by a device according to the independent device claim, an object by a system according to the independent system claim, and an object by a computer program according to the independent computer program claim.

An embodiment of the invention relates to the method according to claim 1, an embodiment to the device according to the independent device claim, an embodiment to the system according to the independent system claim, and an embodiment to the computer program according to the independent computer program claim.

Other embodiments of the invention are described in the dependent claims.

In the method according to an embodiment of the invention for controlling limited-area computer tomography imaging, location data of a first imaging object is determined, reference location data related to the first imaging object is determined, and an imaging area is adjusted based on the location data of the first imaging object and said reference location data for imaging a second imaging object belonging to the object.

The device according to an embodiment of the invention, e.g. a control device or a control unit, for controlling limited-area computer tomography imaging is arranged to determine location data of a first imaging object, determine reference location data related to the first imaging object, and to adjust an imaging area based on the location data of the first imaging object and said reference location data for imaging a second imaging object belonging to the object.

The system according to an embodiment of the invention for controlling limited-area computer tomography imaging, which comprises at least e.g. an X-ray imaging device and a control device or unit integrated or otherwise connected to it, is arranged to determine location data of a first imaging object, determine reference location data related to the first imaging object, and to adjust an imaging area based on the location data of the first imaging object and said reference location data for imaging a second imaging object belonging to the object.

The computer program according to an embodiment of the invention for controlling limited-area computer tomography imaging comprises code means which is arranged to determine location data of a first imaging object, determine reference location data related to the first imaging object, and to adjust an imaging area based on the location data of the first imaging object and said reference location data for imaging a second imaging object belonging to the object.

Terms presented in this document are employed, inter alia, in the following meanings:

An 'object' refers to e.g. an entity, e.g. a human body, skull or jaw area, where objects being imaged, e.g. jaw joints, belong to.

An 'imaging area' refers to e.g. an area where the imaging object is positioned or set automatically whereby, when imaging, the imaging object is positioned in relation to the imaging means as optimally as possible such that a sharp X-ray image is provided with least possible X-ray exposure of the imaging object.

'Location data' refers to e.g. data which relates to a point in the imaging object having been positioned, to be positioned or automatically set in the imaging area from which a limited-area computer tomographic image is to be taken, from which the image is being taken or from which the image has already been taken. Location data is e.g. data presented in three-dimensional coordinates.

'Reference location data' refers to data related to an entity, data related to e.g. a human body, skull or jaw area, which can indicate the relative location of the objects being imaged belonging to the entity, e.g. jaw joints, e.g. their symmetrical location on opposite sides of the body in relation to each other.

According to an example of the invention for controlling limited-area computer tomographic imaging, the location data of a first imaging object is determined when the first imaging object is positioned in the imaging area.

According to an example of the invention, the reference location data related to the first imaging object is determined and the imaging area is adjusted based on the location data of the first imaging object and said reference location data for imaging the second imaging object belonging to the object, whereby the second imaging object is located at a distance determined by the reference location data from the first imaging object.

According to an example of the invention, the reference location data related to the first imaging object is determined and the imaging area is adjusted based on the location data of the first imaging object and said reference location data for imaging the second imaging object belonging to the object, whereby the first and the second imaging object are located symmetrically in relation to the reference location data.

According to an example of the invention, the reference location data related to the first imaging object is determined and the imaging area is adjusted based on the location data of the first imaging object and said reference location data for imaging the second imaging object belonging to the object by limiting the X-ray by a collimator, whereby the first and the second imaging object are located symmetrically in relation to the reference location data.

According to an example of the invention, the first and the second imaging object are imaged in one go during one imaging event.

The method according to the embodiments of the invention speeds up the positioning of the imaging object for limited-area computer tomography imaging, whereby it is sufficient for positioning objects to be imaged located symmetrically on both sides of the body that one of the objects being imaged is positioned in the imaging area. Then, time spent in positioning the imaging area decreases considerably when compared to a situation where both objects to be imaged, e.g. both jaw joints, are separately positioned in the imaging area for imaging.

Furthermore, the method according to the embodiments of the invention simplifies the work flow of computer tomography imaging because, with one imaging area positioning, both objects to be imaged, e.g. imaging objects symmetrically located on both sides of the human body, register comparably to each other, advantageously in the same coordinates, whereby the imaging objects can be compared to each other without additional measures required for image processing or extra accessories by which the images having been imaged in separate coordinates are configured to register comparably to each other in the coordinates.

Additionally, the method according to the embodiments of the invention expands the possible uses of X-ray image data, because X-ray images of both imaging objects are imaged during one imaging event, whereby both imaging objects are together in common coordinates.

According to the invention, to an X-ray image data file are saved e.g. projection images taken of the object to be imaged in X-ray image data format, of which further processing reconstructs three-dimensional X-ray images, and to the X-ray image data file are saved also completed three-dimensional X-ray images and sets of cross-sectional images formed of them for possible further processing.

SHORT DESCRIPTION OF FIGURES

Next, advantageous embodiments of the invention will be described in more detail with reference to the attached drawings, where.

DETAILED DESCRIPTION OF FIGURES

Figure 1:
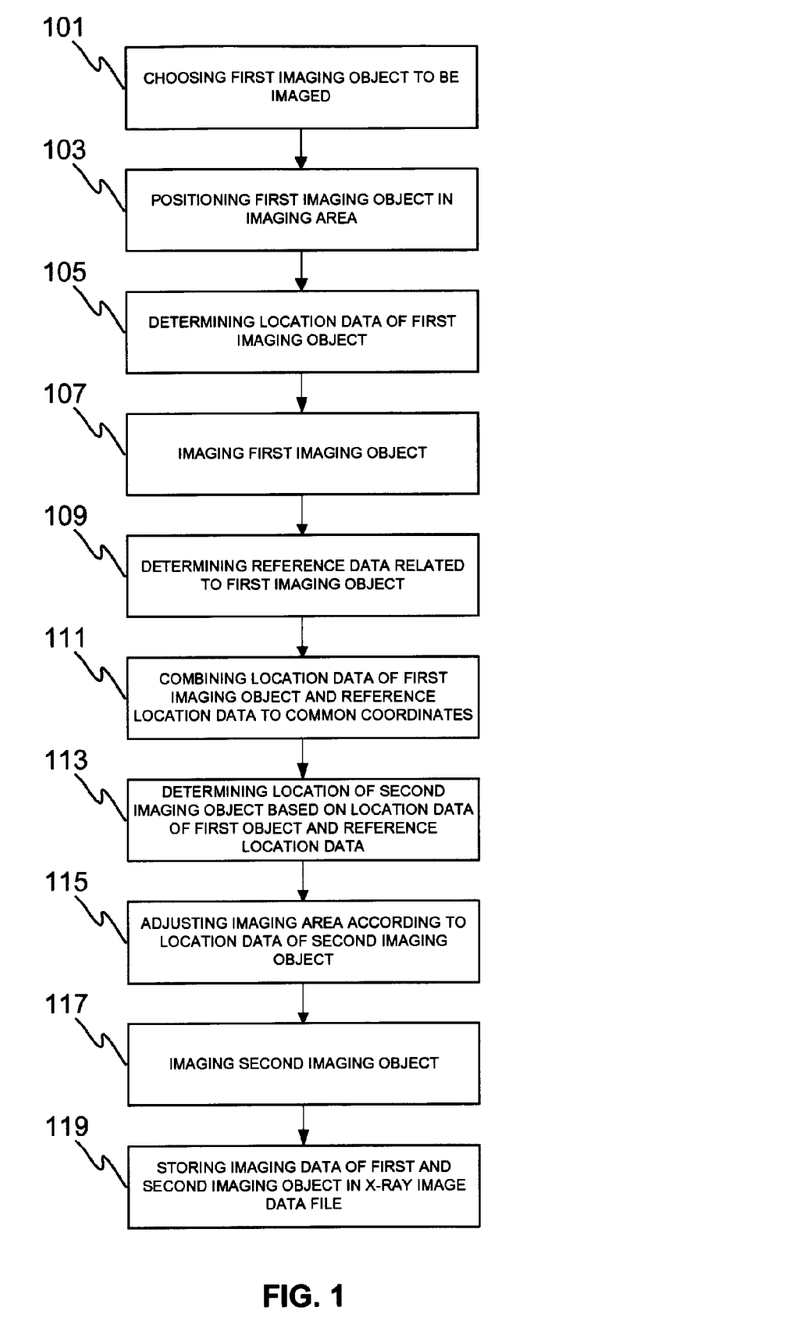
FIG. 1 shows by way of an example a flow chart of a method according to the invention.

FIG. 1 shows a method according to the invention for controlling limited-area computer tomography imaging, where in a starting step (not shown in the figure) the user starts a computer and a computer program operating in it which controls imaging and the imaging apparatus.

In step 101, an imaging object is chosen for imaging, which is typically a part of an object forming a specific entity e.g. a human body, skeleton, skull, jaw area or other equivalent object. The imaging object can be e.g. a jaw joint, a single tooth, a set of teeth or some other part of an object forming an entity.

In step 103, a patient is positioned in relation to the imaging apparatus such that limited-area computer tomography imaging of the chosen imaging object can be performed. The imaging object to be imaged is positioned in an imaging area which is located between a device generating X-rays and a device detecting X-rays. The location of the imaging area is determined by the relative mutual location of the device generating X-rays, the device detecting X-rays and the imaging object in relation to each other, which relative location can be adjusted e.g. in the anteroposterior, lateral and vertical directions.

According to an embodiment, the imaging object is positioned in the imaging area by an object positioning means such that the object positioning means supports e.g. the patient's jaw, neck, forehead, ears or some other equivalent point in the object, whereby the actual imaging object can be positioned precisely and fixedly in the imaging area for computer tomography imaging. The location of the object positioning means is adjustable in relation to the device generating X-rays and the device detecting X-rays e.g. such that the object positioning means, the device generating X-rays and the device detecting X-rays are adjustably supported on e.g. the frame of the imaging apparatus.

In step 105, location data of the imaging object being imaged is determined in the imaging area when the imaging object has been positioned in the imaging area. The location data of the imaging object in the imaging area is determined by the relative mutual location of the device generating X-rays, the device detecting X-rays and the imaging object or the object positioning means in relation to each other, when the imaging object is positioned in the imaging area. The location data of the imaging object in the imaging area can be determined e.g. based on the size and/or diameters of the imaging object, whereby the location data can be associated with e.g. desired points in the imaging object and presented e.g. in three-dimensional coordinates. The location data of the imaging object is proportioned to e.g. the frame of the imaging apparatus or the rotary axis of the supporting arm connecting the device generating X-rays and the device detecting X-rays to each other.

According to an embodiment, the imaging object in the imaging area is pointed by an indicator means and the indicator means indicates the location data of the imaging object. Then, the indicator means senses data related to location and indicates e.g. on a display data related to location, the indicator means being stationary or moving. The data related to location sensed by the indicator means is saved in a memory in the control device. The indicator means can be provided with e.g. a light, laser or equivalent indicator, whereby the indicator can point a desired imaging object or a point of the object the relative location of which in relation to the actual imaging object, e.g. a distance, spacing and/or angle, is known. This way, it is possible e.g. to point the patient's outer auditory canal by the indicator means to determine the location data of the jaw joint in the imaging area, as the jaw joint is very typically at the same point in relation to the outer auditory canal for all people. In this case the jaw joint being positioned in the imaging area, when the indicator means is used for pointing the outer auditory canal, the indicator means indicates the location data of the jaw joint in the imaging area.

According to an embodiment, the location data of the imaging object in the imaging area is determined based on earlier data related to the location of the same imaging object received from the memory of the control device. Then, the indicator of the indicator means can be set automatically to show the location data of the imaging object received from the memory, whereby e.g. a light indication sent by the indicator means intersects the imaging object, e.g. its centre, in the imaging area. According to an example, the indicator means receives from the memory earlier location data related to the same patient's jaw joint, whereby the indicator of the indicator means sets automatically to show the location data received of the jaw joint.

According to an embodiment, the location data of the imaging object in the imaging area is determined based on an earlier image of the same imaging object taken by limited-area computer tomography imaging, intraoral imaging or panoramic imaging. Specification U.S. Pat. No. 6,118,842 describes, inter alia, a dual-purpose imaging apparatus which first takes a panoramic image of the imaging object in the panoramic mode, which is analysed and processed to obtain location data and, after that, the same imaging object can be positioned in the imaging area for limited-area computer tomography imaging based on the location data obtained.

According to some embodiments of the method, step 105 can precede step 103. For instance, the location data of the imaging object is determined and, after that, the imaging apparatus is directed such that the imaging object is positioned in the imaging area.

In step 107, the imaging object in the imaging area is imaged by a limited-area computer tomography apparatus the location data of which has been determined in accordance with steps 103 and/or 105. When the imaging object is in the imaging area, the device generating X-rays and the device detecting X-rays rotate around the imaging object being between them in the imaging area, whereby desired projection images of the imaging object are taken e.g. on each cycle of 180-360 degrees. The whole imaging object in the imaging area can be imaged by a specific number of projection images. The projection images are saved e.g. in X-ray image data format to an X-ray image data file for further processing.

Alternatively in step 107, the imaging object is in the imaging area when the imaging area is adjusted by limiting X-rays by at least one dynamic collimator, whereby the device generating X-rays and the device detecting X-rays rotate around the imaging object being between them in the imaging area such that a rotation centre formed by the device generating X-rays and the device detecting X-rays does not move during imaging between the imaging objects at all. It is also possible to implement the focusing of the imaging area in a combined way where the more precise imaging area is searched by limiting X-rays by at least one dynamic collimator and by moving the rotation centre between the imaging object but for a shorter travel than the full distance of the imaging objects.

In step 109, reference location data related to the location data of the imaging object in the imaging area is determined, when the imaging object is in the imaging area. According to some embodiments of the method, step 109 can precede or succeed step 103 or can be performed as part of step 103.

Reference location data refers to data related to an object, e.g. a human body, skull or jaw area, and, on the other hand, it refers to data belonging to the imaging object being imaged belonging to the object, e.g. a jaw joint. According to an embodiment, the reference location data describes e.g. a symmetry plane, symmetry axis, centre line or equivalent data of the object on different sides of which the imaging objects belonging to the object are located symmetrically. For instance in the human body, there are several such imaging objects. Jaw joints, for example, are located symmetrically on two sides of the symmetry plane of the skull or jaw area. According to an embodiment, the reference location data describes e.g. a distance between imaging objects belonging to the object.

In step 109, reference location data is determined which relates to e.g. the measures or dimensions of the head or skull or some other object. Later, some examples of such measurements will be described. The reference location data can be determined e.g. based on the head or skull width. Then, the reference location data advantageously determines e.g. a distance between desired imaging objects. Alternatively, the reference location data can be advantageously determined before step 103. Then in step 103, the object positioning means supports the object being imaged, e.g. the patient's head, in order to keep it stationary. According to an embodiment, based on the determined reference location data, the indicator means as earlier described points at a point where the imaging object being imaged should be located in order to be in the imaging area, or a point where a specific part of the object, e.g. the nose or jaw, should be located in order for the imaging object being imaged to be in the imaging area. By means of the reference location data, the indicator means indicates the above-mentioned point e.g. by a light, laser or other equivalent indicator. The indicator means indicates data related to location e.g. on the display of the indicator means. The data related to reference location sensed by the indicator means is saved in the memory in the control device.

In step 109, reference location data is determined which relates to e.g. the symmetry plane of the head or skull or some other object. Alternatively, the reference location data can be advantageously determined before step 103. Then in step 103, the object positioning means can be directed based on the reference location data. The object positioning means can support the object being imaged, e.g. the patient's head, at a desired point such that it remains stationary. Alternatively, the object positioning means can be directed e.g. such that the object positioning means supports the object at the point of a plane determined by its reference location data, e.g. symmetry plane, whereby in relation to the plane determined by the reference location data, e.g. symmetry plane, the object is divided symmetrically into two parts.

In step 111, the location data of the imaging object belonging to the object and the reference location data related to the imaging object determined in step 109 are proportioned to each other by the control device.

According to an embodiment, the reference location data is determined by a visual inspection in step 109. For instance the object being the head (skull), a visual inspection can indicate it being divided symmetrically into two parts seen from the front in relation to a plane passing via the nose and the jaw, whereby the plane representing the reference location data is a symmetry plane passing via the nose and the jaw. Respectively, it can be presumed that the jawbones with their teeth and jaw joints is divided symmetrically according to the same plane determined by the reference location data as the head and the skull. For example, each point in the symmetry plane formed by the left and the right jaw joint is at an equal distance from both jaw joints. According to an embodiment, the reference location data is determined by pointing by an indicator means of the above type by a visual inspection e.g. the nose and/or the jaw, whereby the indicator means indicates the reference location data. Then, the indicator means senses e.g. data related to the location of the nose and/or jaw and indicates data related to location e.g. on the display of the indicator means. The data related to reference location sensed by the indicator means is saved in the memory in the control device. The indicator means can be provided with e.g. a light, laser or other equivalent indicator, whereby the indicator can point at the desired point in the object. In step 111, the above-mentioned indicator means pointing the imaging object and the indicator means pointing the reference location data are scaled and calibrated with each other, whereby the location data sensed and displayed by them and saved by the computer are comparable with each other. The object can be directed according to a plane determined by reference location data e.g. such that the object positioning means, e.g. a jaw, forehead, neck and/or other equivalent support, is set to support the object, the head, according to the plane determined by its reference location data, whereby the object positioning means, advantageously its centre line, supports the head at the point of its symmetry plane. Alternatively, the object positioning means can support the object being imaged, the head, at a desired point such that it remains stationary.

According to an embodiment, the reference location data is determined in step 109 by measuring a dimension of the patient's head, e.g. skull width, whereby the reference location data can be determined based on the dimension measured. Advantageously, said dimension measured or data calculatable of it is used as the reference location data. The measurement of the patient's skull width can be performed in many known ways, e.g. by means of lighting measurement. The measurement of the patient's skull width can also be performed in a way described in the document EP1161122. According to an example, the object positioning means comprises at least two support elements which are adjustable to support the patient's head from different sides, e.g. at the point of or above the ears, whereby a distance between the support elements adjustable against each other is denoted by W1. When the support elements are adjusted such that they both are fast in the skull at the widest point of the head, a distance between them i.e. the skull width is denoted by W2. Furthermore, the object positioning means can comprise e.g. a support element supporting the forehead, whereby the support elements form a 'headgear' setting closely on the head, where the support elements are adjustable in relation to each other. Respectively, it is possible to measure a skull height H by adjusting the support elements below the jaw and on the plane of the crown or a skull depth D by adjusting the support elements on the plane of the forehead and the back of the head. Advantageously, said two opposite support elements are connected with sensors which produce an electric signal comparable to the distance W1, H or D and equivalently the width W2, height or depth of the patient's skull to the computer in a way described e.g. in specification EP1161122. For instance, electric signals of different sizes produced by the sensors equal the values of different distances W1. From the measured skull width W2, it is possible to determine the centre line of the skull by dividing it by two. When in step 111 the computer proportions the signal equivalent to the centre line of the object (e.g. skull) with the signal representing the location of the imaging object being imaged (e.g. jaw joint), the reference location data equivalent to the centre line i.e. the symmetry plane of the skull is obtained. In this way, the reference location data can be scaled into the same coordinates with the location data of the imaging object. Advantageously, the support point of the object positioning means, e.g. the support element supporting the forehead of the 'headgear' or the possible jaw support, is directed to support the object (the head) at the point of the above centre line or symmetry plane.

According to an embodiment, reference location data is determined in step 109 by taking an optical image of the object, e.g. the patient, the patient's head or other part, by a camera being connected to the imaging apparatus and by measuring e.g. a dimension of the patient's head, such as the skull width, from the optical image, whereby the reference location data can be determined based on the dimension measured e.g. in a way described above. Advantageously, said dimension measured or data calculatable of it is used as the reference location data. As an aid in determining the reference location data, it is possible to use data on the distance between the camera and the object or some other equivalent data based on which it is possible to measure from the optical image e.g. the width of the patient's head based on which, again, the reference location data can be determined.

According to an embodiment in step 111, based on the reference location data of the object and the location data of the imaging object in the imaging area is determined the location of the imaging object in relation to the reference location data, e.g. the distance of the imaging object from a plane determined by the reference location data. From now on the imaging object in the imaging area in step 103 and its location data are referred to as a first imaging object and location data of a first imaging object. The location data of the first object is determined as described in step 105 and the reference location data related to the first imaging object as described in step 109. In step 111, the location data of the first imaging object, e.g. its centre, in relation to the reference location data is determined, when the patient is positioned such that the first imaging object is positioned in the imaging area, whereby advantageously the support point of the object is focused to support the object (e.g. the head) such that the object remains stationary. According to an example, the support point of the object positioning means is focused to support the object at the point of a plane determined by said reference location data. According to an example, the distance of the first imaging object from a line or plane determined by the reference location data is determined by calculating by the computer. According to an example, the location data of the first imaging object can be determined by means of a distance and an angle from a line or plane determined by the reference location data by calculating by the computer.

According to an embodiment in step 113, the location data of a second imaging object belonging to the object is determined, which second imaging object is located in relation to the first imaging object comparably determined by the reference location data of the object. According to an example, the second imaging object is located at a distance determined by the reference location data in relation to the first imaging object. According to an example, the second imaging object is typically located on the opposite side of a plane determined by the reference location data, e.g. the symmetry plane, in relation to the first imaging object when the first imaging object is in the imaging area. The location data of the second object is obtained e.g. as a distance determined by the reference location data in relation to the location data of the first object (displacement according to distance in relation to said first object). Alternatively, the location data of the second object is obtained e.g. rotating the location data of the first object in a desired way in relation to the reference location data, e.g. symmetrically onto the opposite side of the symmetry line. The location data of the second imaging object can be determined e.g. by projecting the location data of the first imaging object in relation to a line or plane determined by the reference location data. According to an example, the location data of the second imaging object is obtained by projecting the distance of the first imaging object in relation to the line or plane determined by the reference location data on its opposite side (displacement according to distance in relation to said line/plane). According to an example, the location data of the second imaging object is obtained by projecting a position vector describing the distance and the angle of the location data of the first imaging object onto its opposite side from a line or plane determined by the reference location data (rotation according to position vector in relation to said line/plane). Based on the above, it is possible to determine e.g. the distance between the first and the second imaging object and/or the distance of the second imaging object from the centre line of the reference location data and/or the angle of the second imaging object in relation to the centre line of the reference location data.

In a way described above in step 113, the location data of the second imaging object is discovered in relation to the location data and/or reference location data of the first imaging object when the first imaging object is in the imaging area according to step 103. The support point of the object positioning means is focused to support the object (e.g. the head) such that the object remains stationary, whereby the first and the second imaging object are located symmetrically on opposite sides in relation to the reference location data when the first imaging object is in the imaging area.

According to some embodiments, it is possible to determine the location data of the second imaging object determinable in step 113 before determining the location data of the first imaging object occurring in step 105 or simultaneously with determining the location data of the first imaging object occurring in step 105. In other words, determining the location data of the first and the second imaging object is not bound to occur in any specific order. Then advantageously, in step 109 is first determined reference location data which relates to the location data of the first and the second imaging object. For instance, the above skull measurement can determine e.g. the skull width as the reference location data, whereby the location data of the first and the second imaging object are determined based on the skull width. Then, the skull width determines the distance of the first and the second imaging object from each other and the location data of the first and the second imaging object can be determined in a desired order or even simultaneously.

According to an embodiment in step 115, the imaging area is adjusted based on the location data of the second imaging object determined in step 113 such that the second imaging object is positioned in the imaging area. The positioning of the second imaging object in the imaging area for imaging is based on, according to an example, the positioning of the first imaging object in the imaging area (step 103) such that the device generating X-rays and the device detecting X-rays are automatically adjusted in relation to the imaging area, whereby the location of the imaging area for imaging the second object is adjusted with the location data of the first imaging object in relation to the reference data. Then, the imaging area is adjusted based on the location data of the first imaging object and said reference location data for imaging the second imaging object belonging to the object, whereby the first and the second imaging object are located in a desired way in relation to the reference location data, e.g. at a desired distance from each other or symmetrically in relation to the reference location data. Advantageously in step 115, the object being imaged remains set stationary whereby, when adjusting the imaging area, the first and the second imaging object remain stationary. Advantageously in step 115, the object being imaged remains set stationary such that the object positioning means, e.g. the support point of the object positioning means, is focused to support the object at a desired point, e.g. at the point of a line or plane determined by the reference location data. In step 115, the device generating X-rays and the device detecting X-rays move and/or rotate in relation to the object being imaged being stationary such that the imaging area between the device generating X-rays and the device detecting X-rays is positioned at the point of the location data of the second imaging object determined in step 113. In other words, in relation to the imaging of the first imaging object in step 115, the imaging area between the device generating X-rays and the device detecting X-rays moves and/or rotates for a distance between the first and the second imaging object, for a displacement according to the line/plane determined by the reference location data of the distance of the first imaging object onto the opposite side of the line/plane determined by reference location data or in relation to the distance and the angle of the first imaging object for a displacement/rotation according to the line/plane determined by the reference location data onto the opposite side of said line/plane. There is then no need to position the second imaging object separately in the imaging area, but the location of the second object to be imaged is found out based on the location data of the first object and the reference location data related to it, e.g. a distance or the location of a symmetry line.

Alternatively in step 115, the device generating X-rays and the device detecting X-rays rotate in relation to the object being imaged being stationary such that the imaging area between the device generating X-rays and the device detecting X-rays is positioned at the point of the location data of the second imaging object determined in step 113 by limiting X-rays by at least one dynamic collimator. When the imaging area is adjusted by limiting X-rays by at least one dynamic collimator, the device generating X-rays and the device detecting X-rays rotate around the imaging object being between them in the imaging area such that a rotation centre formed by the device generating X-rays and the device detecting X-rays does not move during the adjustment of the imaging area and imaging.

Alternatively, the imaging area can be adjusted with a hybrid solution where the imaging area is focused by limiting by at least one dynamic collimator and by moving the rotation centre formed by the device generating X-rays and the device detecting X-rays during the adjustment of the imaging area and imaging. Then, the rotation centre moves between the imaging objects for some travel but for a shorter travel than the full distance of the imaging objects.

In a corresponding way as in step 107 in connection with the imaging of the first imaging object, in step 117 the second imaging object is imaged after the second imaging object is in the imaging area according to step 115. Advantageously, the imaging area is at the point of the first imaging object when an image is taken of it (step 107) and at the point of the second imaging object when it is taken (step 117). Advantageously, the first (step 107) and the second imaging object (step 117) are imaged at one imaging event.

In step 117, the device generating x-rays and the device detecting X-rays rotate around the imaging object being between them in the imaging area, whereby desired projection images of the imaging object are taken e.g. on each cycle of 180-360 degrees. A three-dimensional image is reconstructed by a computer applicable for image processing from projection images taken from different directions of the imaging object. The completed three-dimensional image consists of 3D picture elements i.e. voxels. The second imaging object in the imaging area can be imaged as a whole with a specific number of projection images which are transferred after imaging to a computer to be reconstructed as a three-dimensional image which can be shown on the display of the computer. The computer calculates the projection images e.g. in three directions being perpendicular against each other, thus forming an integrated three-dimensional image of the imaging area. The three-dimensional processing of the imaging area enables the fact that the imaging object can always be shown from an optimal direction. Advantageously, imaging is based on an X-ray beam sent by the device generating X-rays towards the imaging object in the imaging area, whereby the device detecting X-rays receives the X-ray beam having penetrated the imaging object. For instance, a suitably pulsed beam forms when rotating around the imaging object with each pulse a projection image of which the three-dimensional image is calculated for its part. In this way, three-dimensional images are obtained from the first and the second imaging area with one positioning, e.g. performed in step 103.

According to an embodiment in step 119, the first projection images taken in step 107 being in the X-ray image data format and the second projection images taken in step 117 are saved in the X-ray image data file for further processing. The first projection images taken in step 107 can also be saved whenever after step 107 in the X-ray image data file. Advantageously, the set of projection images is saved in the X-ray image data file. From the sets of projection images saved in the X-ray image data file, three-dimensional X-ray images of the imaging objects are reconstructed by the computer e.g. in ways known in the field. As the location data of the first and the second imaging object are bound to each other in the above way e.g. as distances between them or their distances and angles in relation to the reference location data, the first and the second projection images are saved in the same three-dimensional coordinates as registered either in separate X-ray image data files or a common X-ray image data file. Advantageously, the first and the second imaging object are imaged during one imaging event, whereby the first and the second projection images are together in common coordinates.

Each three-dimensional image saved in the X-ray image data file can be processed further as a set of cross-sectional images. On a freely chosen section plane, a cross-sectional image is determined of a three-dimensional image, e.g. a cylinder. When the three-dimensional X-ray image data of the imaging object is presented as one X-ray image data file or two single X-ray image data files having common coordinates, it is possible to perform measurements between the first and the second imaging object, e.g. measurements of an angle or a distance from the reference plane/line or measurements of distance between the imaging objects. The three-dimensional X-ray image data formed of the first and the second imaging object can also be presented as two X-ray image data files such that they have common coordinates, whereby it is possible to show the cross-sectional images of the first and the second imaging object equivalent to each other at the same time and simultaneously perform measurements between the X-ray image data file in three-dimensional coordinates. Each X-ray image data file consists of several cross-sectional images, whereby the cross-sectional images of the first and the second imaging object corresponding to each other can be examined in a desired way and measurements performed between corresponding cross-sectional images. When the computer tomographic images of the first and the second imaging object are in the same coordinates with the reference location data in the X-ray image data files, the first and the second imaging object can then be examined by means of cross-sectional images determined by freely chosen section planes.

Figure 2:
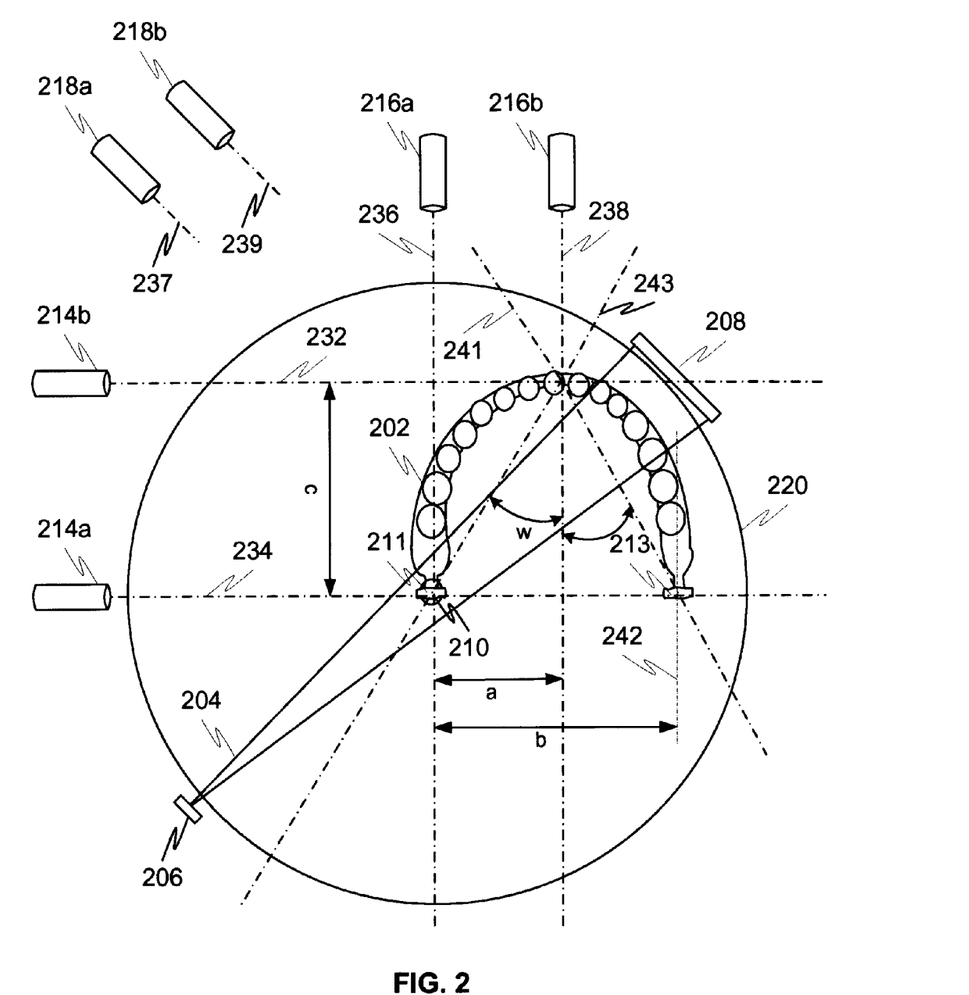
FIG. 2 shows by way of an example a diagram of the jaw area and an imaging arrangement according to the invention in the jaw area.

FIG. 2 shows by means of an example the positioning of a left jaw joint 211 being in a jaw area 202 to an imaging area 210 which is located between a device generating X-rays 206 and a device detecting X-rays 208. When imaging, the device generating X-rays 206 advantageously sends a beam 204 towards the left jaw joint 211 in the imaging area 210, whereby the device detecting X-rays 208 receives an X-ray beam 204 having penetrated the left jaw joint 211. When imaging, the movements of the device generating X-rays 206 and the device detecting them 208 are synchronised such that an image of the imaging area 210 of a desired shape can be saved from the device detecting X-rays 208 in a memory. Advantageously, the device generating X-rays 206 and the device detecting X-rays 208 rotate on a circular orbit 220 synchronised to each other around a rotation axis passing via a centre of the imaging area 210. Advantageously, the device generating X-rays 206 and the device detecting X-rays 208 are attached at the opposite ends of a supporting arm or its parts, which supporting arm or its parts are movably attached to the frame of the imaging apparatus and rotate around its rotation axis. For instance when rotating for 180-360°, image data is taken of the left jaw joint 211 which consist of projection images taken from different directions. When a desired number of projection images have been taken, a three-dimensional image of the left jaw joint 211 is reconstructed of the projection images by the computer, in FIG. 2, the centre of the imaging area 210 is depicted by an intersection of straight lines 234, 236, 237 being perpendicular against each other. The straight line 237 (which is perpendicular against the paper plane) simultaneously depicts the above rotation axis. When the left jaw joint 211 is positioned in the imaging area 210, the intersection of the straight lines 234, 236, 237 detects the location data of the left jaw joint 211 in the imaging area 210. The location data of the left jaw joint 211 is proportioned to the rotation axis (straight line 237) in this case. For a diameter of the imaging area being imaged 210, in which the left jaw joint 211 is imaged, is chosen a desired area around the intersection of the straight lines 234, 236, 237. The left jaw joint 211 in the imaging area 210 can be indicated by an indicator means 214a, 216a, 218a which shows e.g. the centre of the imaging area 210. The indicator means comprises one or more indicators 214a, 216a, 218a, e.g. a laser indicator, which indicate the intersection of the straight lines 234, 236, 237 advantageously in their direction. The indicator 218a indicates the centre of the imaging area 210 in the direction of the rotation axis (straight line 237) (even though drawn on the side of FIG. 2). The imaging apparatus can also comprise at least a second indicator means formed of one or more indicators 214b, 216b, 218b, which can, when desired, indicate some other point in the object than the imaging object e.g. the reference point of the object (e.g. point in the symmetry plane of the jaw area) in the intersection of the straight lines 232, 238, 239. The straight line 239 (which is perpendicular against the paper plane even though drawn on the side of FIG. 2) is parallel with the above rotation axis.

In FIG. 2, the reference location data of the jaw area depicts a plane or a line passing via the intersection formed by the straight lines 232, 238, 239 on different sides of which the left and the right jaw joint 211, 213 belonging to the jaw area 202 locate symmetrically. Above in connection with describing step 109 were depicted various ways to determine the locations of the left jaw joint 211 and the symmetry plane/line in relation to each other and the location of the right jaw joint 213 in relation to the location of the left jaw joint 211 and/or the location of the symmetry plane/line. When e.g. the symmetry plane passing via the intersection formed by the straight lines 232, 238, 239 is used as the reference location data, in FIG. 2 a distance a depicts the distance between the left jaw joint 211 and the symmetry plane and a distance b the distance between the left and the right jaw joint 211, 213, whereby the location data of the right jaw joint 213 can be determined based on the above data. For instance, the distance b can be used as the reference location data. When e.g. the symmetry line passing via the intersection formed by the straight lines 232, 238, 239 is used as the reference location data, in FIG. 2 by means of distances a and c and an angle w between the straight lines 238 and 243 the location of the left jaw joint 211 in relation to the symmetry line can be determined, whereby the location data of the right jaw joint 213 can be determined based on the above data. According to an embodiment, the object, e.g. the patient's head being imaged, is supported for keeping it stationary in a desired way or e.g. at a point determined by the reference location data, e.g. in the middle of the jaw, by an object positioning means, e.g. a jaw support.

Figure 3:
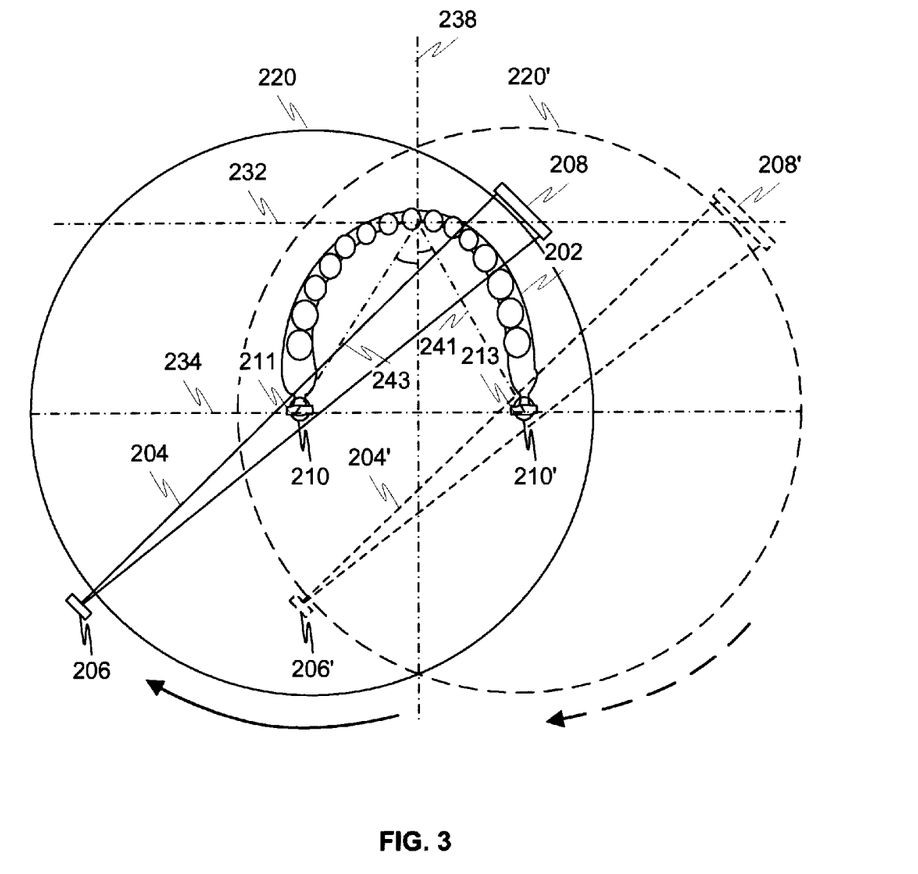
FIG. 3 shows by way of an example a diagram of the jaw area and another imaging arrangement according to the invention in the jaw area.

FIG. 3 shows according to an embodiment the adjustment of the imaging area from a location 210 automatically to a location 210' when, in addition of the imaging of the left jaw joint 211 shown in FIG. 2, wishing to image the right jaw joint 213. Then, the positioning of the right jaw joint 213 in the imaging area 210' is based on the earlier positioning of the left jaw joint 211 in the imaging area 210 and the determining of the location data of the right jaw joint 213 in a way described above. According to an example, the jaw area 202 is supported e.g. by a jaw support or other object positioning means at a desired point or at the point of a symmetry plane/line in order for the jaw joints being imaged remain stationary as precisely as possible during imaging. According to FIG. 3, the displacement and/or rotation of the imaging area from the location 210 to the location 210' is determined based on the location data of the right jaw joint 213, e.g. based on the distances a, b and/or c and/or the angle w depicted in FIG. 2. When imaging the right jaw joint 213 in the imaging area 210', a device generating X-rays 206' and a device detecting X-rays 208' rotate on a circular orbit 220' synchronised to each other around a rotation axis passing via the centre of the imaging area 210'. When imaging, the device generating X-rays 206' advantageously sends a beam 204' towards the left jaw joint 213 in the imaging area 210', whereby the device detecting X-rays 208' receives the X-ray beam 204' having penetrated the left jaw joint 213. For instance when rotating on the circular orbit 220' of 180-360°, image data is imaged of the right jaw joint 213 which consist of projection images taken from different directions. When a desired number of projection images have been taken, a three-dimensional image of the right jaw joint 213 is reconstructed of the projection images by the computer. The projection images taken of the left and the right jaw joint 211, 213 are saved in an X-ray image data file and three-dimensional images are constructed of them by the computer in a way described above (step 119) for further processing.

Alternatively according to another embodiment, the adjustment of the imaging area from the location 210 automatically to the location 210' can be arranged by dynamic collimators, whereby the rotation centre of the supporting arm connecting the device generating X-rays 206 and the device detecting X-rays 208 to each other remains stationary in relation to the frame of the imaging apparatus and rotates around its rotation axis. Alternatively, the imaging area 210, 210' can be adjusted with a hybrid solution where the imaging area is focused by limiting by at least one dynamic collimator and by moving the rotation centre formed by the device generating X-rays 206 and the device detecting X-rays 208 during the adjustment of the imaging area 210, 210' and imaging. Then, the rotation centre moves between the left jaw joint 211 and the right jaw joint 231 for some travel but for a shorter travel than the full distance b of the imaging objects. Advantageously, the first and the second jaw joint 211, 213 are imaged during one imaging event.

Figure 4:
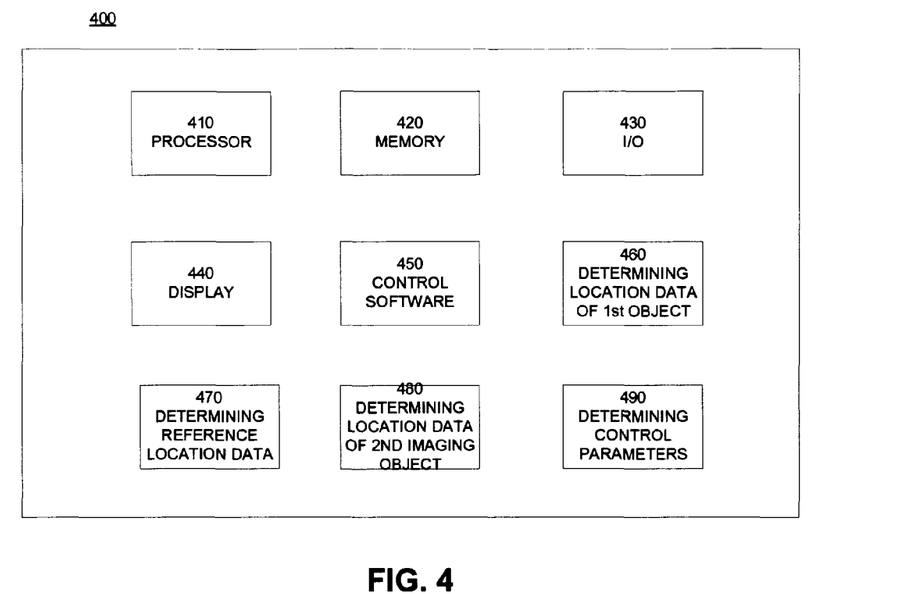
FIG. 4 shows by way of an example a flow chart of a device according to the invention.

FIG. 4 shows a device 400 according to the invention, e.g. a control unit or device, by means of which it is possible to control limited-area computer tomography imaging. The device 400 is advantageously integrated or otherwise connected to the imaging apparatus. The device 400 comprises one or more processors 410 or equivalent programmable controller circuits for performing commands defined by the user and/or software and for processing data related to them. The device 400 comprises one or more external and/or internal memories 420 for saving and storing data, e.g. commands and other information. The device 400 comprises an I/O means 430, e.g. a keyboard, a pointer, an indicator or other user interface e.g. in the control panel, for entering commands, data and other information to the device 400 and/or for receiving them from the device 400 and a display 440 for displaying the commands, data and other information to the user. The device 400 comprises e.g. one or more control softwares 450 in the memory 420 for controlling the imaging apparatus. The control software 450 can also be partially or totally firmware-type device software. Furthermore, the device 400 comprises a means 460 for determining the location data of the first imaging object, a means 470 for determining the reference location data, a means 480 for determining the location data of the second imaging object, and a means 490 for determining control parameters in order to adjust the imaging area according to the location data of the first and/or the second imaging object. Said means 460, 470, 480, 490 operate together with the processor 410 and the memory 420 and at least the means 490 also operates together with the control software 450. Advantageously, the means 460 and the means 470 receive information related to location via the I/O means 430, e.g. indicator means 214a, 216a, 218a and/or indicator means 214b, 216b, 218b shown in FIG. 2. According to an alternative, the means 460 and the means 470 receive information related to location from the memory 420, where is earlier saved information related to the location of the same imaging object e.g. based on earlier performed imagings. According to an alternative, the means 470 receives information related to reference location from a camera (not shown in the figures) being in connection with the imaging apparatus or its memory where there is an image taken of the imaging object at a specific distance, of which it is possible to measure information related to the reference location data, e.g. dimensional data measured of an image taken of the object, such as the patient's head. The memory 420 of the device 400 can also comprise e.g. software related to storing and/or processing X-ray image data.

The control software 450 together with the processor 410 provides that the method according to an embodiment of the invention can be performed in the device 400, e.g. a control device or unit.

According to an embodiment of the invention, the device 400 is arranged to determine the location data of the first imaging object, to determine the reference location data related to the first imaging object and to adjust the imaging area based on the location data of the first object being imaged and said reference location data for imaging the second imaging object. According to an example, the device 460 is arranged to determine the location data of the first imaging object, when the first imaging object is positioned in the imaging area, the means 470 is arranged to determine the reference location data related to the first imaging object, the means 480 is arranged to determine based on the location data of the first imaging object and said reference location data the location data of the second imaging object, and the means 490 is arranged to determine control parameters to adjust the imaging area based on location data of the second imaging object. The means 490 provides the control parameters to the control software 450 which is arranged to adjust the imaging area, e.g. by means of the processor 410 and/or the memory 420 and/or at least one of the means 460, 470, 480, based on the location data of the first imaging object and said reference location data for imaging the second imaging object, whereby the first and the second imaging object are located at a distance from each other determined by the reference location data or symmetrically in relation to the reference location data. The means 490 for adjusting the imaging area according to the location data of the second imaging object comprises determining control parameters e.g. for moving the rotation centre of the supporting arm connecting the device generating X-rays 206 and the device detecting X-rays 208 to each other in relation to the frame of the imaging apparatus. The means 490 can alternatively comprise determining control parameters e.g. for a motor for moving collimators in relation to the rotation centre of the supporting arm connecting the device generating X-rays 206 and the device detecting X-rays 208 to each other such that the rotation centre remains stationary in relation to the frame of the imaging apparatus. The means 490 can alternatively comprise determining control parameters e.g. for a motor for moving the object positioning means in relation to the rotation centre of the supporting arm connecting the device generating X-rays 206 and the device detecting X-rays 208 to each other such that the rotation centre remains stationary in relation to the frame of the imaging apparatus. Advantageously, the first and the second imaging object are imaged during one imaging event.

According to an embodiment of the invention, the device 400 is arranged to adjust the imaging area in relation to the reference location data such that the first and the second imaging object remain stationary for the whole imaging event. Advantageously, the object includes the first and the second imaging object, e.g. the left and right jaw joints 211, 213 belonging to the jaw area 202, whereby the object, e.g. the jaw area 202, is supported stationary e.g. at the point of a plane/line determined by the reference location data, e.g. at the point of a symmetry line passing via an intersection formed by straight lines 232, 238, 239.

According to another embodiment of the invention, the device 400 can be arranged to adjust the imaging area in relation to the reference location data such that first the first imaging object is in the imaging area and then the second imaging object moves to the imaging area. Then, the rotation centre of the supporting arm connecting the device generating X-rays 206 and the device detecting X-rays 208 to each other remains stationary in relation to the frame of the imaging apparatus and rotates around its rotation axis in the imaging situation. Advantageously, the first and the second imaging object are imaged during one imaging event.

According to an embodiment of the invention, the device 400 can be arranged to focus the imaging area by limiting by at least one dynamic collimator and by moving the rotation centre formed by the device generating X-rays and the device detecting X-rays during the adjustment of the imaging area and during the imaging event. Then, the rotation centre moves between the imaging objects for some travel but for a shorter travel than the full distance of the imaging objects.

According to an embodiment of the invention, the device 400 is arranged to adjust the imaging area in relation to the reference location data such that the second imaging object is located symmetrically in relation to the first imaging object at the opposite side of the symmetry plane, symmetry axis or centre line of the object depicting the reference location data.

According to an embodiment of the invention, the device 400 is arranged to adjust the imaging area in relation to the reference location data such that its distance and direction in relation to the reference location data is assessed or measured based on the location data of the first imaging object and the location data of the second imaging object in relation to the reference location data is determined as a projection of the distance and direction of the first imaging object.

According to an embodiment of the invention, the device 400 is arranged to determine the location data of the first imaging object in relation to the reference location data by receiving e.g. by the I/O means 430 an indication indicating the first imaging object or an object located at a specific distance from it, e.g. light or laser indication or other pointer, whereby the indication is provided by indicating by some indicator means 214a, 216a, 218a the first imaging object or an object located at a specific distance from it and/or by indicating by some indicator means 214b, 216b, 218b the reference location data.

According to an embodiment of the invention, the device 400 is arranged to receive e.g. from the memory 420 and/or the I/O means 430 data on the earlier imaged first imaging object and the reference location, based on which the device 400 determines the location data of the first imaging object in relation to the reference location data.

According to an embodiment of the invention, the device 400 comprises a display 440 which is arranged to display the computer tomographic images of the first and the second imaging object as their own single X-ray image data files or as one X-ray image data file, whereby both imaging objects are proportioned to the reference location data.

According to an embodiment of the invention, the device 400 comprises a memory 420 which is arranged to save and store the computer tomographic images of the first and the second imaging object as their own single X-ray image data files or as one X-ray image data file, whereby both imaging objects are proportioned to the reference location data. The memory 420 can comprise for processing X-ray image data one or more image processing software which are arranged to process e.g. with the processor 410 several projection images and X-ray image data files consisting of several projection images. An external or internal computer, which comprises one or more image processing softwares for processing X-ray image data, advantageously receives X-ray image data files consisting of projection images saved in the memory 420 and reconstructs three-dimensional X-ray images of them. The three-dimensional images of the first and the second imaging object corresponding to each other and cross-sectional images formed of them can be examined in a desired way by the computer and measurements performed between corresponding three-dimensional images. The measurements can also be performed with cross-sectional images corresponding to each other. The X-ray image data file consists of projection images, of which the image processing software stored in the memory 420 and/or the image processing software stored in the memory of a computer intended for image processing is arranged e.g. to reconstruct three-dimensional X-ray images e.g. for displaying on the display 440. The image processing software is arranged, e.g. by means of the processor 410 and/or the memory 420, to perform by means of X-ray image data files measurements between the first and the second imaging object. Measurements between the X-ray image data file can be performed simultaneously as the three-dimensional images and/or cross-sectional images of the first and the second imaging object equivalent to each other are examined.

According to an advantageous embodiment, each X-ray image data file consists of several cross-sectional images, whereby in the X-ray image data files the computer tomographic images of the first and the second imaging object are in the same coordinates with the reference location data, whereby the first and the second imaging object can be examined by means of freely chosen cross-sectional images determined by the section levels.

Figure 5:
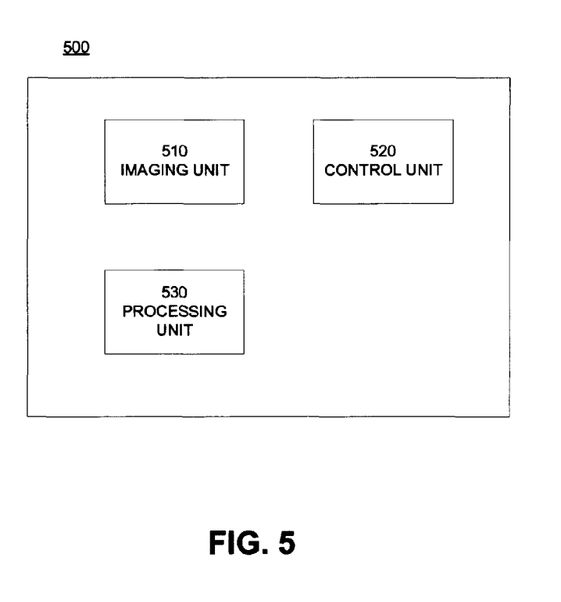
FIG. 5 shows by way of an example a flow chart of a system according to the invention.

FIG. 5 shows a system 500 according to the invention by means of which it is possible to control limited-area computer tomography imaging. The system 500 comprises a control device 520 of the above type including e.g. a processor or a micro controller, a memory, an I/O means, e.g. a control panel, and a display. The control device 520 further comprises a control software, a means for determining location data of a first imaging object, a means for determining reference location data, a means for determining location data of a second imaging object, and a means for determining control parameters in order to adjust the imaging area according to the location data of the second imaging object. The control device 520 including e.g. a processor or a micro controller, where is stored the control software, is advantageously integrated to an imaging apparatus 510. Furthermore, the system 500 comprises an imaging apparatus 510 which is by wire or wirelessly in data communication with the control device 520. The imaging apparatus 510 comprises the device generating X-rays 206 and the device detecting X-rays 208 which are attached at the opposite ends of the supporting arm or its parts, which supporting arm or its part is movably attached to the frame of the imaging apparatus and rotates around its rotation axis. Advantageously, the imaging apparatus 510 comprises an object positioning means, which is adjustably attached to the frame of the imaging apparatus such that the object being imaged, which includes the first and the second imaging object, can be supported at a desired point or e.g. at the point of the reference location data to a position where the first imaging object is in the imaging area. Advantageously, the object includes the first and, the second imaging object, e.g. the left and right jaw joints 211, 213 belonging to the jaw area 202, whereby the jaw support operating as the object positioning means is arranged to support the jaw area 202 at a suitable point or e.g. at the point of a plane/line determined by the reference location data. The object positioning means can also comprise at least two support elements which are adjustable to support the patient's head on different sides, whereby the patient's skull width can be measured as described above in connection with the 'headgear'. Advantageously, the imaging apparatus 510 comprises indicator means 214a, 216a, 218a and/or indicator means 214b, 216b, 218b which are attached to the imaging apparatus 510 and (the indication) shown by which is proportioned e.g. to the frame of the imaging apparatus 510 and/or the rotation axis of the rotating supporting arm connecting the device generating X-rays 206 and the device detecting X-rays 208. Furthermore, the system 500 can comprise an image processing unit 530 e.g. for processing X-ray image data and reconstructing as three-dimensional images as described above.

Advantageously, the imaging apparatus 510 comprises the device generating x-rays 206 and the device detecting X-rays 208 which rotate around the first imaging object 211 in the imaging area 210, whereby desired projection images of the first imaging object 211 are taken e.g. on each cycle of 180-360 degrees. The control device 520 determines in a way described above the reference location data by the means 470 based on the location data of the first imaging object 211 determined by the means 460 and, after that, the location data of the second imaging object 213 by the means 480. The control device 520 determines in a way described above by the means 490 control parameters for the imaging apparatus 510, whereby the control device 520 adjusts the location of the device generating X-rays 206 and the device detecting X-rays 208 such that they rotate around the second imaging object 213 in the imaging area 210', whereby desired projection images of the second imaging object 211 are taken e.g. on each cycle of 180-360 degrees. Alternatively, the control device 520 adjusts the location of collimators limiting X-rays such that the device generating X-rays 206 and the device detecting X-rays 208 rotate around the second imaging object 213 in the imaging area 210', whereby desired projection images of the second imaging object 211 are taken. Advantageously, the first and the second imaging object 211, 213 are imaged at a single positioning of the object to be imaged. Advantageously, the first and the second imaging object 211, 213 are imaged successively during one imaging event. When the first and the second imaging object 211, 213 are imaged, the object being imaged remains stationary e.g. by means of the object positioning means in the imaging apparatus 510. Alternatively, the object being imaged moves such that first the first imaging object 211 and then the second imaging object 213 is in the imaging area. The object being imaged can be moved by means of the object positioning means.

According to an embodiment of the invention, the system 500 is arranged to determine the location data of the first imaging object, to determine the reference location data related to the first imaging object and to adjust the imaging area based on the location data of the first object being imaged and said reference location data for imaging the second imaging object, whereby the first and the second imaging object are located at a distance determined by the reference location data from each other or symmetrically in relation to the reference location data.

According to an embodiment of the invention, a computer program for controlling limited-area computer tomography imaging is arranged to perform at least part of the steps 105, 109, 111, 113, 115 and 119 of the method illustrated in FIG. 1 when the computer program (control software) is run in the device 400, e.g. the control device 520, e.g. the processor or micro controller.

According to an embodiment of the invention, the computer program comprises a code means which is arranged to determine the location data of the first imaging object, to determine the reference location data related to the first imaging object and to adjust the imaging area based on the location data of the first object being imaged and said reference location data for imaging the second imaging object, whereby the first and the second imaging object are located at a distance determined by the reference location data from each other or symmetrically in relation to the reference location data.

According to an embodiment of the invention, the computer program comprises a code means which is arranged to adjust the imaging area in relation to the reference location data such that the first and the second imaging object remain stationary for the whole imaging.

According to an embodiment of the invention, the computer program comprises a code means which is arranged to adjust the imaging area in relation to the reference location data such that the second imaging object is locate symmetrically in relation to the first imaging object at the opposite side of the symmetry plane, symmetry axis or centre line of the object describing the reference location data.

According to an embodiment of the invention, the computer program comprises a code means which is arranged to adjust the imaging area in relation to the reference location data such that assessing or measuring based on the location data of the first imaging object its distance and direction in relation to the reference location data and determining the location data of the second imaging object in relation to the reference location data as a projection of the distance and direction of the first imaging object.

According to an embodiment of the invention, the computer program comprises a code means which is arranged to determine the location data of the first imaging object in relation to the reference location data by receiving an indication indicating the first imaging object or an object located at a specific distance from it.

According to an embodiment of the invention, the computer program comprises a code means which is arranged to determine the location data of the first imaging object in relation to the reference location data by receiving data of the earlier imaged first imaging object and the reference location.

According to an embodiment of the invention, the computer program comprises a code means which is arranged to display the computer tomographic images of the first and the second imaging object as their own single X-ray image data files or as one X-ray image data file, whereby both imaging objects are proportioned to the reference location data.

According to an embodiment of the invention, the computer program comprises a code means which is arranged to store the computer tomographic images of the first and the second imaging object as their own single X-ray image data files or as one X-ray image data file, whereby both imaging objects are proportioned to the reference location data. Advantageously, each X-ray image data file consists of several cross-sectional images, whereby the cross-sectional images of the first and the second imaging object correspond to each other can be examined in a desired way and, measurements performed between corresponding cross-sectional images. Advantageously, the computer program comprises a code means which is arranged to perform measurements between the first and the second imaging object by means of three-dimensional images of the first and the second imaging object constructed of X-ray image data files. Advantageously, each X-ray image data file consists of several cross-sectional images, whereby in the X-ray image data files the computer tomographic images of the first and the second imaging object are in the same coordinates with the reference location data, whereby the first and the second imaging object can be examined by means of freely chosen cross-sectional images determined by the section levels.

Above were described only some embodiments of the arrangement according to the invention. The principle of the invention can naturally be varied within the scope defined by the claims e.g. for the part of implementation details and utilisation areas.

The invention claimed is:

1. A method for controlling limited-area computer tomography imaging, comprising
    determining location data of a first imaging object belonging to an object, the object having a symmetry plane, the step of determining location data comprising at least one of:
        a. analyzing an image of the object to determine the location data of the first imaging object is in an imaging area, and
        b. estimating the location data of the first imaging object based on an external anatomic characteristic of the object,
    determining a first rotation axis of a first imaging area based on the location data of the first imaging object, the first imaging area including the first imaging object, the first rotation axis having a first distance from the symmetry plane,
    computer-tomography imaging the first imaging area,
    determining a second rotation axis of a second imaging area based at least on a location of the first rotation axis, the second rotation axis having a second distance from the symmetry plane, the second distance being approximately equal to the first distance, and
    computer-tomography imaging the second imaging area.

2. The method according to claim 1, wherein the second imaging area includes a second imaging object.

3. The method according to claim 2, wherein the first and the second imaging object remain stationary during and between the steps of computer-tomography imaging the first and second imaging areas.

4. The method according to claim 2, wherein the second imaging object is located symmetrically in relation to the first imaging object on the opposite side of the symmetry plane, a symmetry axis or a centre line of the object.

5. The method according to claim 1, further comprising receiving data of an earlier imaged first imaging object and a reference location wherein the step of determining the location data of the first imaging object further comprises determining the location data in relation to the reference location data.

6. The method according to claim 1, further comprising displaying and/or storing computer tomographic images of the first and the second imaging object as their own single X-ray image data files or as one X-ray image data file, whereby both imaging objects are proportioned to the reference location data.

7. The method according to claim 6 wherein each X-ray image data file comprises a plurality of cross-sectional images, whereby the cross-sectional images of the first and the second imaging object correspond to each other and measurements performed between corresponding cross-sectional images.

8. The method according to claim 6, further comprising performing measurements by means of X-ray image data files between the first and the second imaging object.

9. The method according to claim 6, wherein each X-ray image data file comprises a plurality of cross-sectional images, whereby in the X-ray image data files the computer tomographic images of the first and the second imaging object are in the same coordinates with the reference location data, whereby the first and the second imaging object can be examined by means of cross-sectional images determined by freely chosen section levels.

10. The method according to claim 1, wherein the step of determining location data comprises at least one of:
    estimating the location data of the first imaging object based on a location of an auditory canal of the object; and
    estimating the location data of the first imaging object based on a width of the object.

11. An apparatus comprising:
    means for determining location data of a first imaging object belonging to an object, the object having a symmetry plane, the means for determining location data comprising at least one of:
        a. means for analyzing an image of the object to determine the location data of the first imaging object is in an imaging area, and
        b. means for estimating the location data of the first imaging object based on an external anatomic characteristic of the object,
    means for determining a first rotation axis of a first imaging area based on the location data of the first imaging object, the first imaging area including the first imaging object, the first rotation axis having a first distance from the symmetry plane,
    means for controlling limited-area computer-tomography imaging the first imaging area,
    means for determining a second rotation axis of a second imaging area based at least on a location of the first rotation axis, the second rotation axis having a second distance from the symmetry plane, the second distance being approximately equal to the first distance, and
    the means for controlling limited-area computer-tomography imaging the second imaging area.

12. The apparatus according to claim 11, wherein the second imaging area includes a second imaging object.

13. The apparatus according to claim 12 wherein means for computer-tomography imaging is configured to image the first and second imaging areas with the first and the second imaging object remaining stationary during and between imaging of the first and second imaging areas.

14. The apparatus according to claim 12, wherein the means for determining a second rotation axis is configured to estimate that the second imaging object is located symmetrically in relation to the first imaging object on the opposite side of the symmetry plane, a symmetry axis or a centre line of the object.

15. The apparatus according to claim 11, further comprising means for receiving data of an earlier imaged first imaging object and a reference location wherein the means for determining the location data of the first imaging object is further configured to determine the location data in relation to the reference location data.

16. The apparatus according to claim 11, further comprising means for displaying and/or storing computer tomographic images of the first and the second imaging object as their own single X-ray image data files or as one X-ray image data file, whereby both imaging objects are proportioned to the reference location data.

17. The apparatus according to claim 16, wherein each X-ray image data file comprises a plurality of cross-sectional images, whereby the cross-sectional images of the first and the second imaging object correspond to each other and measurements performed between corresponding cross-sectional images.

18. The apparatus according to claim 16, further comprising means for performing measurements by means of X-ray image data files between the first and the second imaging object.

19. The apparatus according to claim 16, wherein each X-ray image data file comprises a plurality of cross-sectional images, whereby in the X-ray image data files the computer tomographic images of the first and the second imaging object are in the same coordinates with the reference location data, whereby the first and the second imaging object can be examined by means of cross-sectional images determined by freely chosen section levels.

20. The apparatus according to claim 11, wherein the means for determining location data comprises at least one of:
means for estimating the location data of the first imaging object based on a location of an auditory canal of the object; and
means for estimating the location data of the first imaging object based on a width of the object.

21. A system comprising:
a control apparatus being connected to communicate with an imaging apparatus,
the control apparatus configured to determine location data of a first imaging object belonging to an object, the object having a symmetry plane, the apparatus being configured to perform at least one of:
a. analyzing an image of the object to determine the location data of the first imaging object is in an imaging area, and
b. estimating the location data of the first imaging object based on an external anatomic characteristic of the object,
the control apparatus configured to determine a first rotation axis of a first imaging area based on the location data of the first imaging object, the first imaging area including the first imaging object, the first rotation axis having a first distance from the symmetry plane,
the control apparatus configured to control the imaging apparatus to perform limited-area computer-tomography imaging the first imaging area,
the control apparatus configured to determine a second rotation axis of a second imaging area based at least on a location of the first rotation axis, the second rotation axis having a second distance from the symmetry plane, the second distance being approximately equal to the first distance, and
the control apparatus configured to control the imaging apparatus to perform limited-area computer-tomography imaging the second imaging area.

22. The system according to claim 21, wherein the second imaging area includes a second imaging object.

23. The system according to claim 22, further configured to image to image the first and second imaging areas with the first and the second imaging object remaining stationary during and between imaging of the first and second imaging areas.

24. The system according to claim 22, further configured to estimate that the second imaging object is located symmetrically in relation to the first imaging object on the opposite side of the symmetry plane, a symmetry axis or a centre line of the object.

25. The system according to claim 21, further configured to receive data of an earlier imaged first imaging object and a reference location wherein the system is further configured to determine the location data in relation to the reference location data.

26. The system according to claim 21, further configured to display and/or store computer tomographic images of the first and the second imaging object as their own single X-ray image data files or as one X-ray image data file, whereby both imaging objects are proportioned to the reference location data.

27. The system according to claim 26, wherein each X-ray image data file comprises a plurality of cross-sectional images, whereby the cross-sectional images of the first and the second imaging object correspond to each other and measurements performed between corresponding cross-sectional images.

28. The system according to claim 26, further configured to perform measurements by means of X-ray image data files between the first and the second imaging object.

29. The system according to claim 26, wherein each X-ray image data file comprises a plurality of cross-sectional images, whereby in the X-ray image data files the computer tomographic images of the first and the second imaging object are in the same coordinates with the reference location data, whereby the first and the second imaging object can be examined by means of cross-sectional images determined by freely chosen section levels.

30. The system according to claim 21, wherein the system is configured to perform at least one of:
estimating the location data of the first imaging object based on a location of an auditory canal of the object, and
estimating the location data of the first imaging object based on a width of the object.

* * * * *